(12) United States Patent
Richards et al.

(10) Patent No.: US 7,896,401 B2
(45) Date of Patent: Mar. 1, 2011

(54) RESPIRATORY GAS HUMIDIFIER ADAPTER WITH PRESSURE RELIEF VALVE AND AUDIBLE SIGNAL GENERATOR

(75) Inventors: Fredrick M. Richards, Plymouth, MA (US); Gregory S. King, Cazenovia, NY (US); Robert Simas, Jr., Norfolk, MA (US)

(73) Assignee: Smiths Medical ASD, Inc., Keene, NH (US)

( * ) Notice: Subject to any disclaimer, the term of this patent is extended or adjusted under 35 U.S.C. 154(b) by 849 days.

(21) Appl. No.: 11/682,726

(22) Filed: Mar. 6, 2007

(65) Prior Publication Data

US 2008/0216830 A1    Sep. 11, 2008

(51) Int. Cl.
*F16L 35/00* (2006.01)
(52) U.S. Cl. .......................................... 285/93; 285/386
(58) Field of Classification Search .................... 285/93; 137/853; 261/DIG. 65
See application file for complete search history.

(56) References Cited

U.S. PATENT DOCUMENTS

| | | | | |
|---|---|---|---|---|
| 1,854,518 | A | * | 4/1932 | Little .................... 137/516.15 |
| 2,275,937 | A | * | 3/1942 | Baker .................... 137/516.15 |
| 2,473,912 | A | * | 6/1949 | Schwinn .................... 137/853 |
| 2,918,895 | A | | 12/1959 | Buell |
| 3,783,590 | A | * | 1/1974 | Allen .......................... 96/419 |
| 3,807,445 | A | | 4/1974 | McPhee |
| 3,916,818 | A | | 11/1975 | Barr et al. |
| 4,036,919 | A | | 7/1977 | Komendowski et al. |
| 4,045,525 | A | | 8/1977 | Huggins |
| 4,100,235 | A | | 7/1978 | Thornwald |
| 4,134,940 | A | | 1/1979 | Sherman |
| 4,149,556 | A | * | 4/1979 | Schwabe .................... 137/115.01 |
| 4,171,007 | A | * | 10/1979 | Bouteille .................... 137/601.19 |
| 4,247,844 | A | | 1/1981 | Zapolski et al. |
| 4,350,647 | A | | 9/1982 | de la Cruz |
| 4,367,182 | A | | 1/1983 | Kienholz |
| 4,915,879 | A | | 4/1990 | Weiler et al. |

FOREIGN PATENT DOCUMENTS

GB            1441320            6/1976

* cited by examiner

*Primary Examiner* — Aaron Dunwoody
(74) *Attorney, Agent, or Firm* — Luedeka, Neely & Graham, PC

(57) ABSTRACT

A pressurized respiratory gas humidifier adapter with a pressure relief valve having an audible signal generating device incorporated into a low-flow respiratory gas supply system at a position in the system wherein the pressure relief valve and an audible signal generating device are protected from inadvertent damage during use of the humidification system, especially during connection of the adapter into the respiratory gas supply system and when the adapter is connected to a humidifier container prior to coupling into the gas supply system. The pressure relief valve and audible signal generator are incorporated into a humidifier adapter for creating a hermetic seal with a standard medical humidifier container, and the pressure relief valve relieves and regulates the pressure in the humidified gas supply system when an obstruction in the gas flow path to the patient occurs, while generating an audible sound emitted at a predetermined pressure threshold level throughout a desired respiratory gas flow-rate range.

6 Claims, 3 Drawing Sheets

RESPIRATORY GAS HUMIDIFIER ADAPTER WITH PRESSURE RELIEF VALVE AND AUDIBLE SIGNAL GENERATOR

FIELD OF THE INVENTION

This invention relates in general to respiratory therapy and treatment devices, and, in particular, to inhalation therapy devices.

BACKGROUND OF THE INVENTION

In the administration of respiratory therapy or in respiratory treatment, particularly such as in the administration of inhalation therapy, a breathable gas such as, for example, air or oxygen, or a mixture of breathable gases such as, for example, a mixture of air, oxygen and helium, are administered to a patient to assist the patient in breathing. Such treatment is used for treating emphysema or asthma and other lung and respiratory diseases, as well as for postoperative treatment and cardiac patient care. During such treatment it is desirable to add moisture to the treating gas so as to prevent desiccation of the respiratory tract or membranes during treatment, especially over a long period of time. To this end moisture is added to the breathable gas or gases which results in the humidification of the breathable gases.

During the administration of such humidified respiratory gases, if the gas supply to a patient becomes partially blocked, or totally occluded, pressure increases in the humidified gas supply system. Such a pressure increase or blockage can reduce or stop the administration of the inhalation therapy to the patient, and if the pressure increases sufficiently a rupture of the humidified gas supply system can occur. Accordingly, it is desirable that the humidified respiratory gas supply system include a pressure relief system to guard against pressure build-up to a level which can cause a rupture in the humidified gas supply system, and that the pressure relief system include an alarm so that a healthcare provider or clinician will be alerted to this condition.

While provisions for pressure relief and audible signals to indicate a blockage in a humidified gas supply system are known to those skilled in the art, many such devices require high respiratory gas flow rates to cause a reliable audible tone to be generated. Such devices are unsuitable for use in a low flow humidified gas supply system wherein it is intended that the humidified respiratory gases be administered at a flow rate of between about 0.5 liters per minute to about 15 liters per minute such as used, for example, for neonatal patients. At such low flow rates such known devices do not reliably generate an audible tone to alert a clinician that a blockage has occurred.

SUMMARY OF THE INVENTION

The present invention is directed to overcoming one or more of the problems or disadvantages associated with the relevant technology. As will be more readily understood and fully appreciated from the following detailed description of a preferred embodiment wherein a pressurized respiratory gas humidifier adapter with a pressure relief valve having an audible signal generating device is incorporated into a low-flow respiratory gas supply system at a position in the system wherein the pressure relief valve and audible signal generating device are protected from inadvertent damage during use of the humidification system, especially during connection of the adapter into the respiratory gas supply system and when the adapter is connected to a humidifier container prior to coupling into the gas supply system. The pressure relief valve and audible signal generator are incorporated into a humidifier adapter for creating a hermetic seal with a standard medical humidifier container, and relieve and regulate the pressure in the humidified gas supply system when an obstruction in the gas flow path to the patient occurs, while effecting an audible sound emitted at a predetermined pressure threshold level throughout a desired respiratory gas flow-rate range.

DESCRIPTION OF THE DRAWINGS

Further objectives of the invention, together with additional features contributing thereto and advantages accruing therefrom, will be apparent from the following description of a preferred embodiment which is shown in the accompanying drawings, wherein.

DETAILED DESCRIPTION OF A PREFERRED EMBODIMENT

Figure 1:
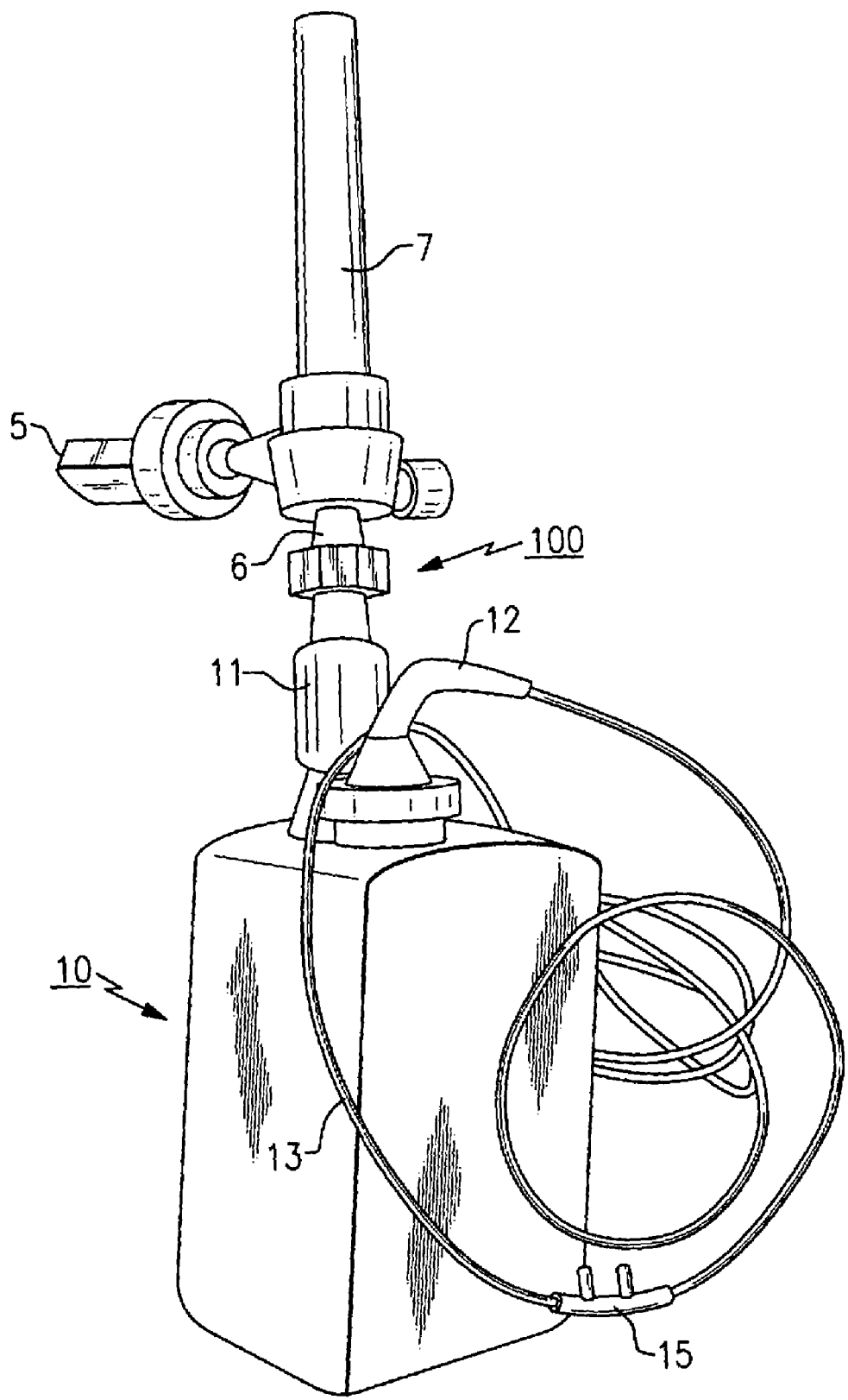
FIG. 1 is a perspective view of an illustrative embodiment of our invention in an application environment.
Figure 2:
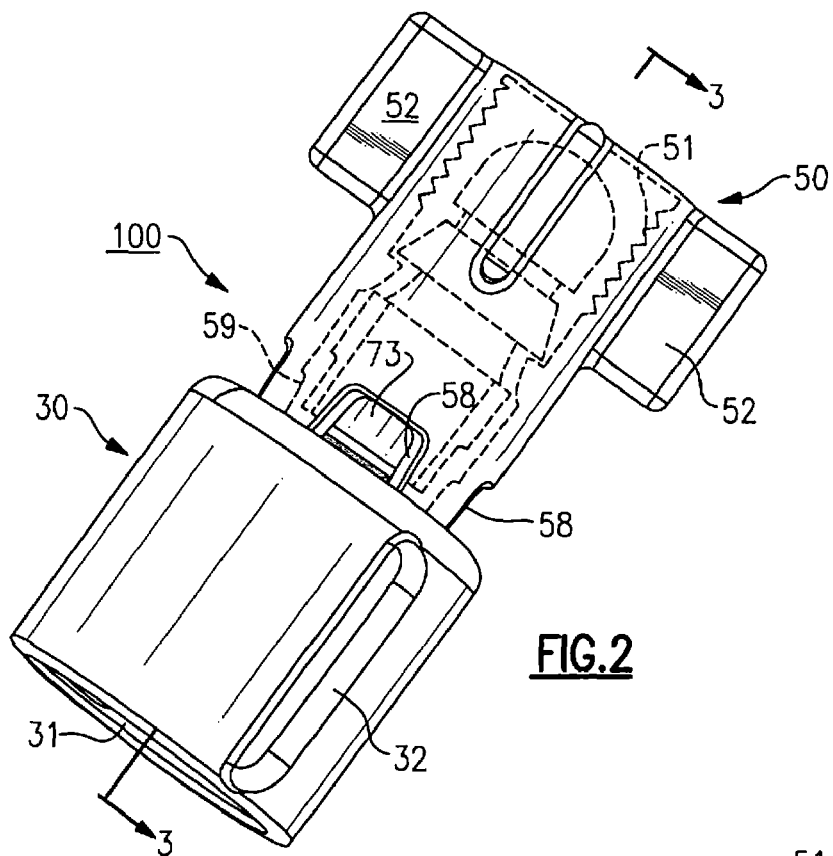
FIG. 2 is an enlarged perspective view of a pressurized respiratory gas humidifier adapter having a pressure relief valve incorporated therein which produces an audible signal upon the occurrence of a respiratory gas pressure exceeding a predetermined threshold level.

Referring now to the drawings, there is illustrated in FIG. 1 a preferred embodiment of the invention incorporated into a low-flow humidified respiratory gas supply system. A suitable supply of pressurized respiratory gas 5, such as found in hospitals or supplied by suitable pressurized tanks, is coupled to a standard externally threaded discharge outlet 6 under the control of a pressure regulator 7 for providing a suitable source of respiratory gas for use by a patient receiving such therapy. To humidify such respiratory gas, a standard hermetically sealed medical humidifier container 10, containing a quantity of suitable sterile humidification medium, is positioned to receive through an inlet 11 the pressurized respiratory gas being supplied from the supply of pressurized respiratory gas 5 to the humidifier container 10.

The humidifier container 10 has a inlet 11 through which the respiratory gas is passed over or through the sterile humidification medium for absorbing moisture before being passed from the humidifier container 10 to a patient. The humidified respiratory gas is then passed from the humidifier container 10 out through an outlet port 12, and is conveyed through suitable tubing 13 to be administered to a patient by means of a nose cannula 15, as illustrated, a mask or other suitable delivery device.

There is illustrated in FIG. 1, and in greater detail in FIGS. 2-5, a humidifier adapter 100 which is coupled in fluid communication between the discharge outlet 5 of the pressurized respiratory gas supply and the external threaded inlet 11 of the humidifier container 10. The humidifier adapter 100 comprises three functional components: 1) an internally threaded adapter body 30 for engaging the external threads of the humidifier container inlet 11 and forming a connection therewith; 2) an internally threaded oxygen nut assembly 50 which forms a sealed connection with the externally threaded discharge outlet 5 of the pressurized respiratory gas supply; and 3) a tone generating sleeve 70 which relieves pressure in the respiratory gas supply system when the pressure therein exceeds a predetermined threshold level, and generates an audible warning signal so that a healthcare provider or clinician will be alerted to this condition.

Figure 3:
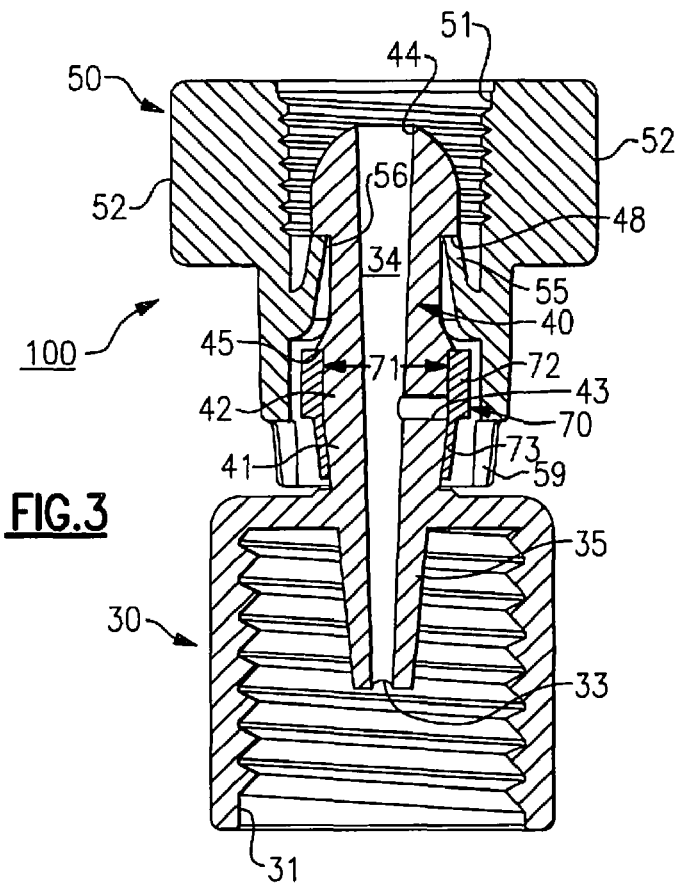
FIG. 3 is a cross-sectional view of the illustrative embodiment of our invention taken in the general direction of lines 3-3 of FIG. 2.
Figure 4:
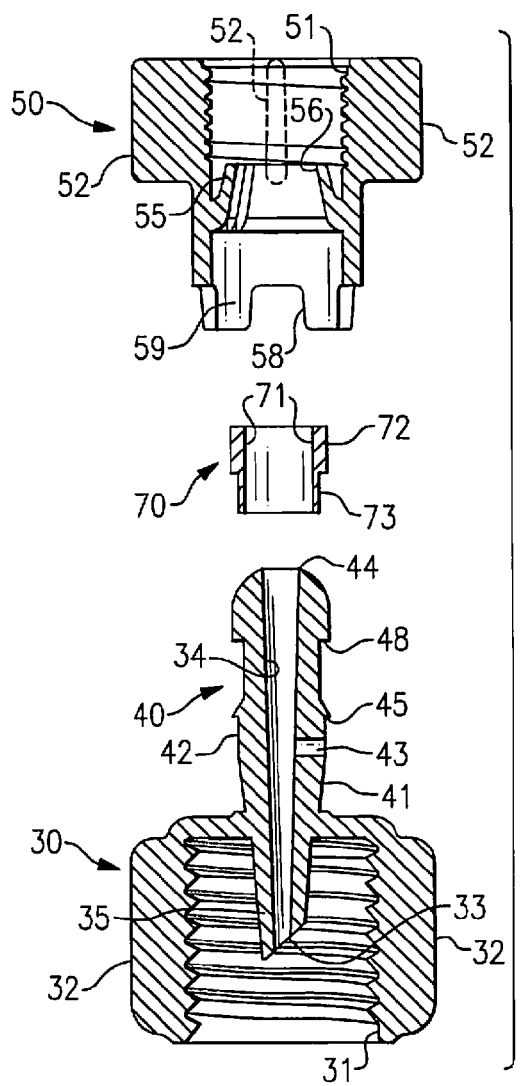
FIG. 4 is an exploded view of the cross-section of the illustrative embodiment as shown in FIG. 3.

As best illustrated in FIGS. 3 and 4, the adapter body 30 has an internally threaded cavity 31 having a diameter for receiving the external threads of the inlet 11 of a standard humidifier container 10. To this end, the adapter body includes a pair of outwardly extending wing tabs 32 spaced opposite to each other for facilitating the threading of the adapter body 30 onto and into engagement with the humidifier container 10. As is known to those skilled in this art, the humidifier container 10 contains a seal covering the inlet opening 11 to the humidification medium contained therein. Accordingly, the seal covering must be broken in order to access the medium contained therein. To this end the adapter body 30 is formed with an internally extending piercing lance 35 having a tapered passage 34 formed there through and which punctures the seal covering on the humidifier container 10 as the adapter body is threaded into engagement with the humidifier container inlet opening 11 for passing respiratory gas through an opening 33 in the tip of the lance 35 into the humidifier container 10.

Extending outwardly from the top of the adapter body 30 is a vertically extending stem 40 having a tapered portion 41 which forms a part of the audible signal generator. The outermost diameter of the tapered portion 41 terminates in a cylindrical portion 42, and at the joinder of the tapered portion 41 and the cylindrical portion 42 a through-hole 43 extends from the outer surface of the stem 40 into the tapered passage 34 which extends from the opening 33 of the lance 35 to the top 44 of the stem 40. The through-hole 43 functions as a passage way to relieve excess pressure and assists in the generation of the audible signal when the respiratory gas system pressure exceeds a predetermined threshold level.

Figure 5:
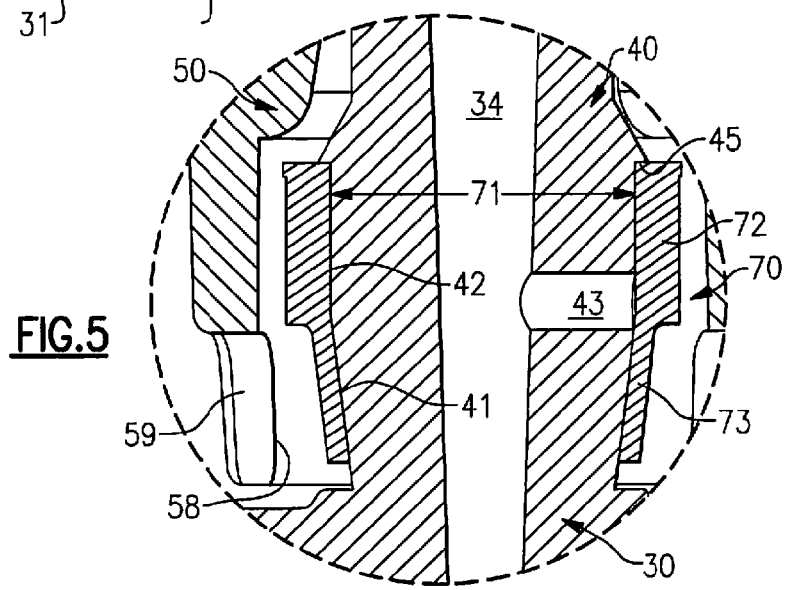
FIG. 5 is an enlarged partial sectional view of pressure relief valve to better illustrate the tone signal generating portion thereof.

Referring particularly to FIGS. 3-5, a silicone sleeve 70 is carried about the cylindrical portion 42 and tapered portion 41 of stem 40. While the sleeve 70 has a substantially uniform internal diameter 71, the external diameter thereof is stepped. The portion 72 of the sleeve surrounding the cylindrical portion 42 of the stem 40 and extending across the through-hole 43 is of a thickness sufficient to secure the sleeve 70 onto the cylindrical portion 42 of the stem 40. The portion 73 of the sleeve surrounding the tapered portion 41 of the stem 40 is thinner, such as approximately 0.02 inches. The thicker portion 72 of the sleeve is positioned about the cylindrical portion 42 of the stem with a terminal end thereof abutting against a tapered stepped abutment 45 circumferentially formed about the stem 40. The thinner portion 73 of the sleeve overlies the tapered portion 41 of the stem 40 and in response to respiratory gas passing through the through-hole 43 will generate an audible signal as excess respiratory gas pressure is relieved through the through-hole 43. In operation, while the present system is especially useful in relieving the pressure in a low flow rate respiratory gas system, in other systems the diameter of the through-hole 43, the respiratory gas flow rate, the threshold relief pressure and thicknesses of the silicone sleeve 70 may be varied depending upon the results sought for the generation of an audible signal.

The oxygen nut assembly 50 has an internally threaded cavity 51 having a diameter for receiving the external threads of the discharge outlet 6 of the pressurized respiratory gas supply for forming a sealed connection therewith. To this end, the oxygen nut assembly 50 includes a plurality of outwardly extending wing tabs 52 equally spaced circumferentially about the outer periphery of the portion of the oxygen nut assembly 50 which is adjacent to the entry into the internal threaded cavity 51 for facilitating the threading of the oxygen nut assembly 50 into sealed engagement with the respiratory gas discharge outlet 6.

To connect the oxygen nut assembly 50, which is connected to the respiratory gas discharge outlet 6, with the adapter body 30, which is connected to the humidifier container 10, the interior of the internal cavity 51 is formed with a retainer ring 55 for locking the top distal end 44 of the stem 40 into the oxygen nut assembly 50 in a proper position to engage the respiratory gas discharge outlet 6 with the tapered passage 34. As best illustrated in FIGS. 3 and 4, the oxygen nut assembly 50 passes over and about the distal end 44 of the stem 40 of the adapter body 30 which is received through an opening 56 formed by the retainer ring 55. The stem 40 is thereby locked into engagement when the distal end 44 of the stem 40 passes through the opening 56 in the retainer ring 55, and the retainer ring 55 locks behind the stem 40 in an undercut abutment 48 formed on the stem 40. This produces a loose fit of the oxygen nut assembly 50 about the stem 40, thereby connecting the two portions together while allowing each to be freely rotatable relative to the other for facilitating their individual coupling to components of the respiratory gas system and the unimpeded discharge of excess respiratory gas pressure through and around castellated openings 58 formed in a skirt portion 59 of the oxygen nut assembly 50.

Positioning the humidifier adapter 100, and consequently the internal pressure relief valve and audible signal generator structure in this manner, in line between the humidifier container 10 and the discharge outlet 6 of the pressurized respiratory gas supply 5, prevents the pressure relief valve and the audible signal or tone generator structure from being grasped or used as a lifting point by a clinician when carrying a humidifier container 10 as heretofore a prevalent, but undesirable, practice with other systems used for pressure relief and or excess pressure signal generation. In this manner, the pressure relief valve and audible signal generator structure are protected from inadvertent damage during use of the humidification system, especially during connection of the humidifier adapter 100 to the discharge outlet 6 of the respiratory gas supply system.

While this invention has been described in the specification and illustrated in the drawings with reference to a preferred embodiment, the structure of which has been disclosed herein, it will be understood by those skilled in the art to which this invention pertains that various changes may be made and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims.

This application was prepared without reference to any particular dictionary. Accordingly, the definition of the terms used herein conforms to the meaning intended by the inventors acting as their own lexicographer, in accordance with the teaching of the application, rather that any dictionary meaning which is contrary to or different from the inventors' meaning regardless of the authoritativeness of such dictionary.

What is claimed is:

1. An adapter for coupling a source of pressurized respiratory gas to a container for holding a quantity of liquid to be administered to a patient as a humidified respiratory gas, the adapter comprising:
   an adapter body having a first and a second end with a tapered passage formed therethrough, said tapered passage tapering toward said second end;
   said adapter body having a stem with a tapered portion tapering toward said second end which forms a part of an audible signal generator, a largest diameter of the tapered portion terminates into a cylindrical portion, and a through-hole extends from an outer surface of said stem into said tapered passage;
   said through-hole forming a passage way to relieve excess pressure and assist in the generation of the audible signal when the respiratory gas system pressure exceeds a predetermined threshold level;
   a substantially uniform internal diameter sleeve carried about said cylindrical portion and said tapered portion of said stem, a portion of said sleeve surrounding said cylindrical portion of said stem and extending across said through-hole, a portion of said sleeve surrounding said tapered portion of said stem being thinner than said portion of said sleeve surrounding said cylindrical portion of said stem, said thinner portion of said sleeve overlies said tapered portion of said stem and in response to respiratory gas passing through said through-hole generates an audible signal as excess respiratory gas pressure is relieved.

2. The adapter for coupling a source of pressurized respiratory gas to a container for holding a quantity of liquid to be administered to a patient as a humidified respiratory gas of claim 1 wherein said sleeve is positioned coaxially with said stem and to discharges the excess pressure respiratory gas in the same direction as the taper of said tapered passage formed through said adapter body.

3. The adapter for coupling a source of pressurized respiratory gas to a container for holding a quantity of liquid to be administered to a patient as a humidified respiratory gas of claim 1 further including a nut assembly having a plurality of outwardly extending wing tabs for facilitating the formation of a sealed connection between said adapter body and the source of pressurized respiratory gas.

4. The adapter for coupling a source of pressurized respiratory gas to a container for holding a quantity of liquid to be administered to a patient as a humidified respiratory gas of claim 3 wherein said wing tabs are equally spaced circumferentially about the outer periphery of said nut assembly.

5. The adapter for coupling a source of pressurized respiratory gas to a container for holding a quantity of liquid to be administered to a patient as a humidified respiratory gas of claim 1, wherein thinner portion of said sleeve is formed by an inwardly stepped external diameter portion of said sleeve.

6. The adapter for coupling a source of pressurized respiratory gas to a container for holding a quantity of liquid to be administered to a patient as a humidified respiratory gas of claim 1 wherein a distal end of said tapered stem portion forms a container seal piercing lance.

* * * * *